United States Patent [19]
Robinson

[11] B 3,982,095
[45] Sept. 21, 1976

[54] RESPIRATORY HUMIDIFIER

[75] Inventor: Thomas C. Robinson, Berkeley, Calif.

[73] Assignee: Searle Cardio-Pulmonary Systems Inc., Emeryville, Calif.

[22] Filed: Oct. 4, 1973

[21] Appl. No.: 403,507

[44] Published under the second Trial Voluntary Protest Program on February 10, 1976 as document No. B 403,507.

[52] U.S. Cl. .............................. 219/273; 128/193; 219/275; 219/362; 219/433; 261/122; 261/142; 261/DIG. 65

[51] Int. Cl.² ................ H05B 1/00; A61M 15/00; B01F 3/04

[58] Field of Search .......................... 219/271–276, 219/362, 459, 438, 333, 432, 433; 137/202, 423, 430; 261/141, 142, 122, 123, 121 R, DIG. 65; 128/186, 192, 194

[56] References Cited
UNITED STATES PATENTS

| | | | |
|---|---|---|---|
| 1,116,931 | 11/1914 | Schutt | 137/202 |
| 1,373,072 | 3/1921 | Holmberg | 137/202 X |
| 1,664,333 | 3/1928 | Taylor | 261/122 X |
| 2,082,363 | 6/1937 | Stone | 261/123 |
| 2,164,881 | 7/1939 | Meyerson | 128/192 |
| 3,659,604 | 5/1972 | Melville et al. | 219/272 UX |
| 3,757,082 | 9/1973 | Goicoechea | 219/271 |
| 3,804,280 | 4/1974 | Van Amerongen et al. | 128/194 X |
| 3,806,102 | 4/1974 | Valemta et al. | 261/122 X |
| 3,864,440 | 2/1975 | Goicoechea | 219/271 X |

FOREIGN PATENTS OR APPLICATIONS

| | | | |
|---|---|---|---|
| 269,045 | 11/1929 | Italy | 219/438 |
| 487,396 | 12/1938 | United Kingdom | 261/122 |

*Primary Examiner*—A. Bartis
*Attorney, Agent, or Firm*—Lothrop & West

[57] ABSTRACT

A respiratory humidifier has a base with a thermally controlled heater therein effective to heat a first transfer surface on the top of the base. Removably pressed against the first transfer surface is a second transfer surface forming the bottom of a container into which liquid is admitted, close to the bottom, by a float valve to establish a liquid level. Gas is admitted to the container below the liquid level through an inlet tube and is released from the container above the liquid level through an outlet tube. A porous pad in the container is in the gas flow path between the inlet tube and the outlet tube to provide extended, wettable surface. A float blocks the entrance to the outlet tube when the liquid level rises unduly and a normally closed shunt passage between the inlet tube and the outlet tube opens by differential pressure when the entrance to the outlet tube is blocked.

8 Claims, 4 Drawing Figures

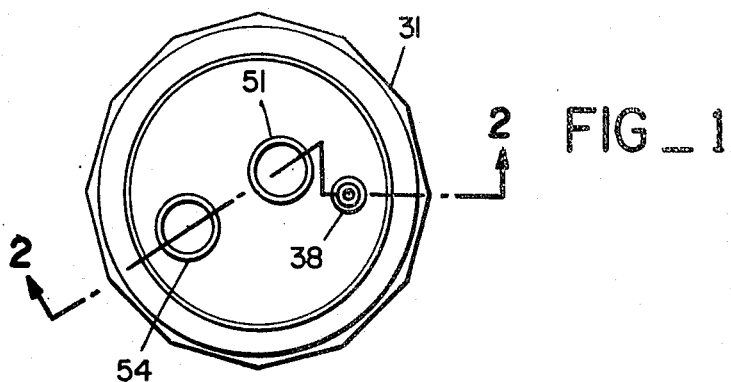
FIG_1
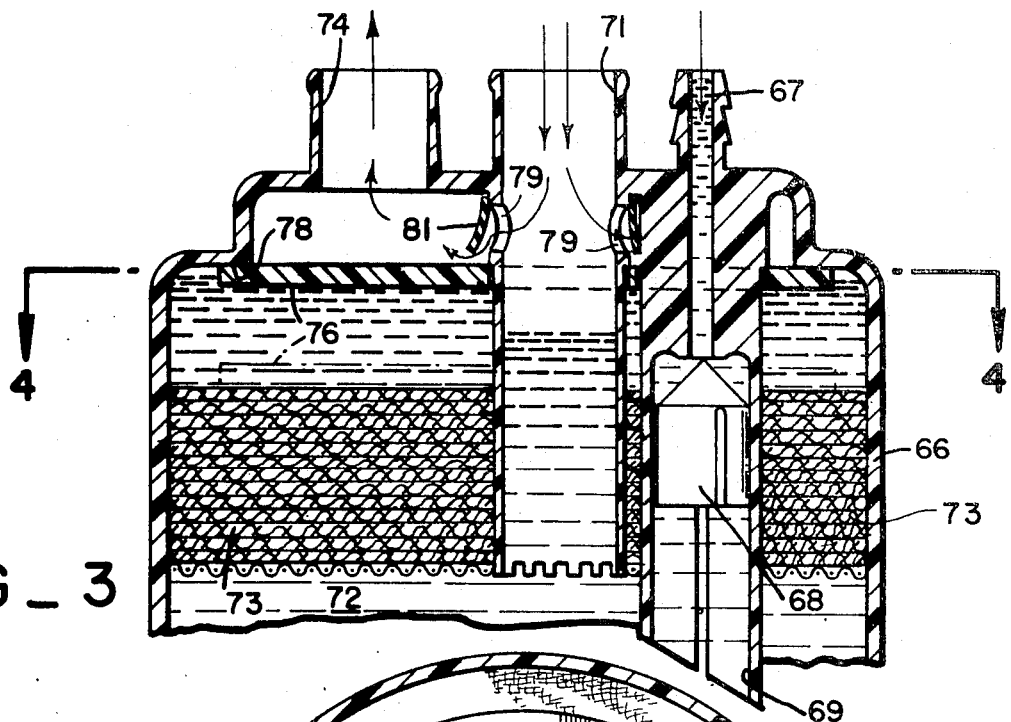
FIG_3
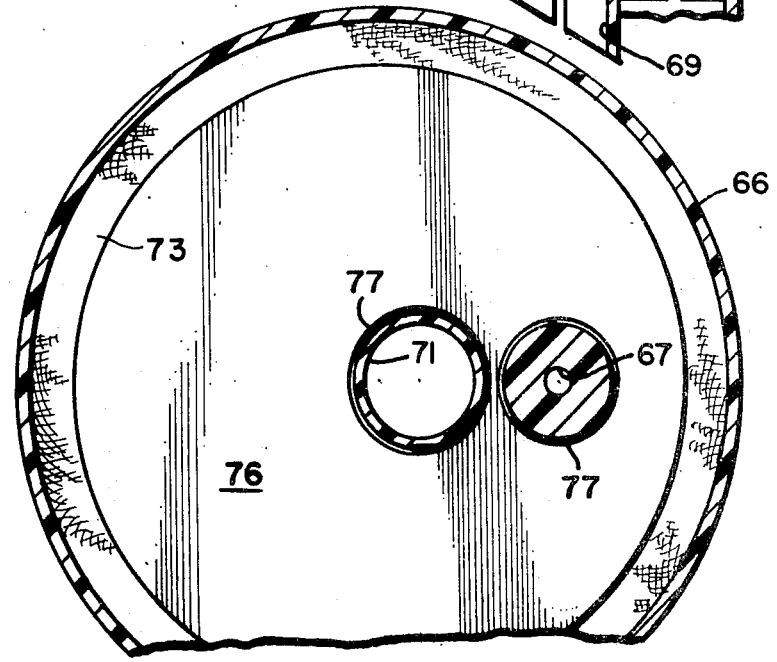
FIG_4

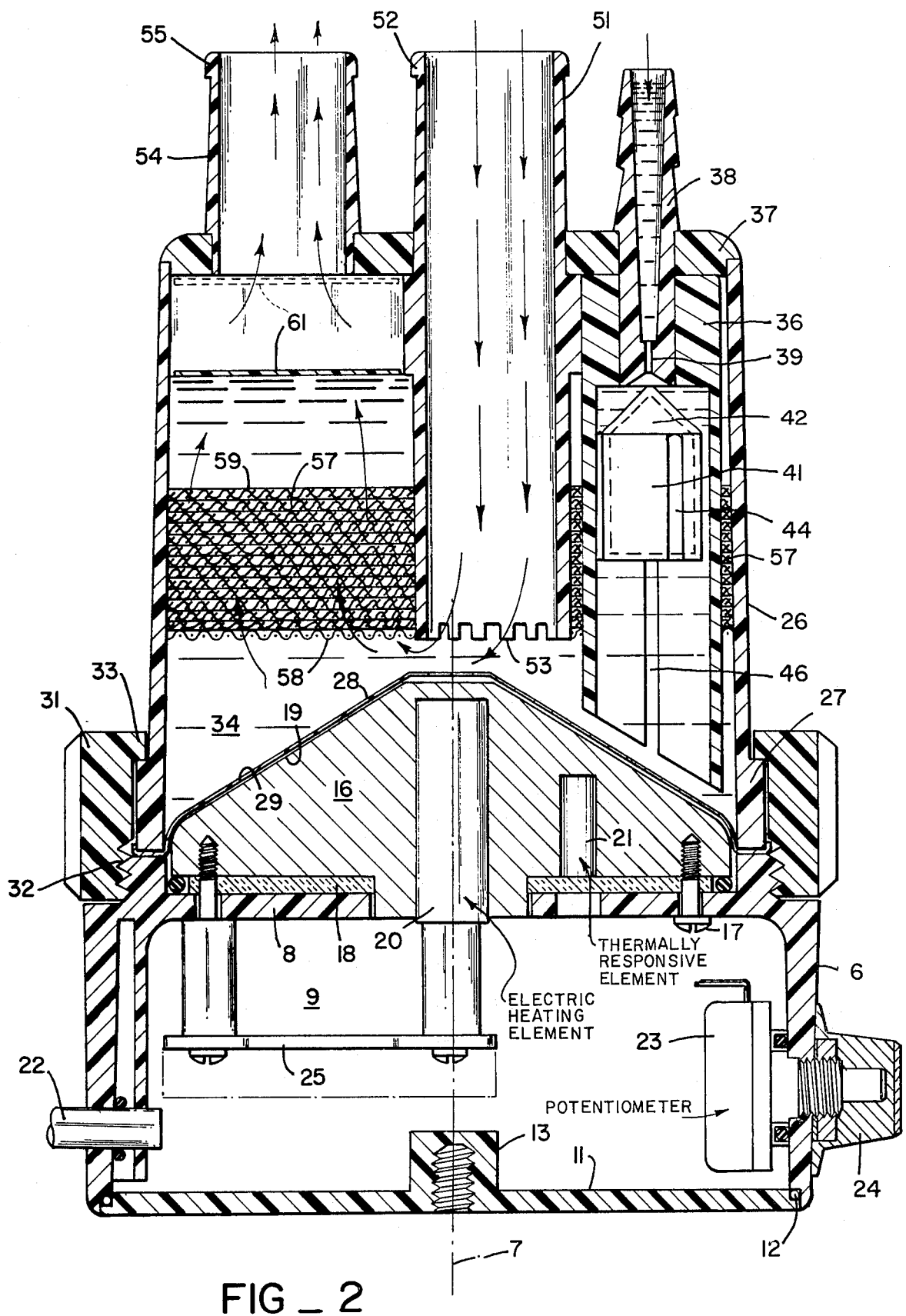
FIG_2

RESPIRATORY HUMIDIFIER

In the treatment of patients it is often necessary to employ mechanism for conducting breathing in an artificial or partially artificial fashion. The gas used for breathing, usually atmospheric air often mixed with oxygen or with other materials, is preferably maintained at a particular, favorable humidity or is supplied with adjunct material such as medication deemed beneficial to the patient. It is highly desirable to provide a mechanism which can reliably supply the necessary or desired humidity or an appropriate moisture content under treatment conditions.

It is therefore an object of the invention to provide a respiratory humidifier that is readily maintained in a sanitary and effective condition without skilled supervision.

Another object of the invention is to provide a respiratory humidifier in which the desired liquid in evaporated form is added to the inspirated gas.

Another object of the invention is to provide a respirator humidifier that affords a highly uniform addition of previously liquid material to gas for inspiration.

Another object of the invention is to provide a respiratory humidifier which does not endanger the patient in the event the humidifier for any reason should fail.

Another object of the invention is to provide a respiratory humidifier which is readily utilized in connection with existing respiratory equipment.

A further object of the invention is to provide a respiratory humidifier that can easily, economically and effectively be provided.

A further object of the invention is in general to provide an improved respiratory humidifier.

Other objects, together with the foregoing, are attained in the embodiments of the invention described in the accompanying description and illustrated in the accompanying drawings, in which:

FIG. 1 is a plan of the humidifier;

FIG. 2 is a cross-section on several planes through a typical form of respiratory humidifier pursuant to the invention, the section planes being indicated by the lines 2 — 2 of FIG. 1;

FIG. 3 is a view comparable to FIG. 2 but with portions broken away, showing a modified form of humidifier container structure; and FIG. 4 is a cross-section, the plane of which is indicated by the line 4—4 of FIG. 3.

In summary, the invention embodiments attain the above objects of the invention by affording a respiratory humidifier including a base supporting a heater having a first heat transfer surface against which is pressed a second, complementary heat transfer surface on a container. Liquid is conducted into the container to a lower location therein near the second heat transfer surface and rises to maintain a selected level of liquid in the container under float control. Gas is also admitted to the interior of the container near the second heat transfer surface below the liquid level and is released from the container away from the second heat transfer surface and at an upper location above the selected liquid level. There is a pad in the container disposed between the lower location and the upper location and extending substantially completely across the container. The pad is permeable throughout to the liquid and to the gas, provides an extended surface for wetting by the liquid and has its upper surface substantially coincident with the selected liquid level.

While a respiratory humidifier pursuant to the invention can be embodied in a large number of different forms, it has with good effect been incorporated as disclosed herein.

In the example illustrated in FIGS. 1 and 2, there is provided a base 6, usually a circular-cylindrical molded member symmetrical about a vertical axis 7. The base includes an integral transverse wall 8 defining a chamber 9 which is substantially closed by a base plate 11 properly secured in place against a seal 12 so that the chamber 9 is isolated from the environment. If desired, the base plate can have a fastening boss 13 to receive a fastener to attach the base to any selected support, although the base can stand on a table or the like without being secured.

Mounted on and included in the base is a heater 16. This preferably is a block of heat-conducting material piloted into the wall 8 and secured in place by fastenings 17. An intervening insulating disc 18 inhibits thermal flow between the block 16 and the compartment 9. The heater block 16 is preferably formed as the frustum of a cone to define a conical first heat transfer surface 19 effective quickly to transfer heat. The block 16 is heated by a heating element 20 embedded in the block along the axis 7 and supported on a wiring board 25 mounted within the compartment 9.

Also embedded in the block 16 is a thermally responsive element 21, such as a thermistor, wired in a convenient fashion with the heating element 20 to a cable 22 entering through the base from a suitable source of power and connected to supply electricity to the heating element 20. Also mounted on the base and partly housed within the compartment 9 is a potentiometer 23 with an external control knob 24 appropriately connected in the circuit to the heating element 20. By manual control the heating element can be connected in the circuit or disconnected therefrom and under the influence of the heat responsive device 21 will maintain substantially any chosen temperature in the block 16 of the heater.

Detachably mounted on and supported by the base 6 is a container 26. This is generally an inverted, cup-like member conveniently molded of plastic and generally of tapered or circular-cylindrical form symmetrical about the axis 7. The container 26 at its lower end has a peripheral, outstanding flange 27 adapted to rest on a part of the base 6. The container is closed at the bottom by a conical, metallic bottom wall 28 of substantially the same contour as the top of the block 16 so as to afford a second heat transfer surface 29 complementary to the surface 19.

To secure the parts detachably together for use there is provided a ring 31 having threads 32 engaging comparable threads on the base 6 and also having an inturned rim 33 adapted to bear against the flange 27 and thus urge the surfaces 19 and 29 as nearly as possible into tight abutment. To make sure of good heat transfer between the two surfaces, and intervening space can be occupied by a good heat transfer liquid such as one of the appropriate silicone compounds.

The container 26 including the bottom wall 28 encloses a compartment 34 into which extends a liquid supply tube 36 mounted on the top 37 of the container 26, preferably by means of a liquid connection tube 38. The tube has a conically stepped outside contour to receive a rubber tube or other appropriate conductor of liquid, usually water. The tube 38 enters into the tube 36 and preferably is reduced to afford a small regulating orifice 39 against which operates a float valve 41. This is in the form of a closed, hollow body having a conical valve top 42 and of somewhat smaller diameter than the interior of the tube 36. Ribs 44 on the outside of the float valve act as float guides within the tube 36 and allow incoming liquid to pass around the float.

The effect of the float is to maintain as nearly as possible a fixed level of liquid within the compartment 34 approximately at the level of the conical top 42 of the float valve. Liquid entering the tube 36 from above travels around the float valve and is released from the tube 36 close to the bottom thereof which extends into close proximity to the second heat transfer surface 29. Some of the incoming liquid, however, can escape from the tube 36 before passing under the bottom thereof by flowing through a slot 46 therein. In this fashion a controlled supply of liquid is brought into close juxtaposition with the heat transfer surface 29.

Also entering through the top 37 of the container 26 is a gas inlet tube 51 which extends well down into the compartment 34 into close juxtaposition with the surface 29. The tube 51 has a beaded entrance 52 for the attachment of an appropriate flexible hose or the like supplying the gas to be breathed. The inlet tube 51 near its lower end is provided with castellations 53 so that air flowing in through the tube can escape therefrom in a number of different locations in order to bubble up in various places through the liquid in the compartment 34.

Also mounted on the cover 37 and affording passage from the compartment 34 outwardly is an outlet tube 54 having a beaded rim 55 for the reception of an outflow flexible tube. At its other end the tube 54 has an opening 56 into the upper portion of the compartment 34 at a location quite remote from the secondary surface 29 and well above the water level in the compartment. Air can thus travel from the tube 51 through the compartment 34 and out through the tube 54.

Particularly pursuant to the invention there is provided a pad 57 constructed to be permeable to the water and to the gas. The pad affords an extended, wettable surface to assist in transferring the liquid into the gas, preferably by evaporation. Conveniently, the pad 57 is made up of a number of superposed, annular layers of a woven fabric loosely tied together into an integral unit. The pad 57 is perforated to receive the tubes 36 and 51 and extends from its bottom face 58 well below the water line to an upper surface 59 which may be coincident with or slightly below the liquid level. The pad is oif a size virtually the same as the interior of the container 26 so that the pad can easily be pressed into place and by friction will stay in an appropriate location just above the bottom of the tube 51.

The liquid in the compartment 34 wets all of the surfaces of the pad and air or gas traveling from the tube 51 toward the tube 54 must necessarily pass through the pad. Thus, any large air bubbles which might otherwise occur are effectively broken up into very small bubbles. This effectively increases the interface area between the flowing gas and the contained liquid.

For normal operation the heater 20 is in effect. The incoming fluids, both liquid and gaseous, are brought into close proximity to the heating surface 29 and have their temperatures raised to or maintained at a selected value. This assists in the vaporization of the liquid and its entrainment by the outgoing air. The net result is the provision of appropriately humidified or medicated gas flowing through the outlet 54 to the patient.

Since a device of this sort should be as nearly as possible failsafe, provision is made to prevent flow of liquid to the patient should the float valve 41 by any chance become stuck in an open position and thus admit a continuous flow of water or liquid medication to the compartment 34. This might eventually rise well above the normal liquid level and flow out through the gas discharge tube 54. For that reason there is provided in the compartment 34 a floating spider 61 or plate of material which is buoyant on the liquid and which is normally substantially spaced from the entrance of the tube 54. Air flow is thus normally around and between the spider arms of the float 61 which normally simply rests on the subjacent pad 57. However, should the liquid level rise inordinantly the float 61 rises with the liquid until a local disc portion of the spider float eventually overlies the entrance to the tube 54. This blocks any flow of liquid into that tube and furthermore closes the compartment 34 except for the opening through the tube 51. While excess liquid can flow into the tube 51 under emergency conditions, the patient is protected since there cannot be any liquid flow into the tube 54.

As another embodiment of this portion of the structure, the base and the connections and the like being as previously described, there is afforded a device as shown in FIGS. 3 and 4. In this instance the container 66 is substantially as before with a liquid inlet 67 controlled by a float valve 68 and having an inlet tube 69 extending toward the heater base. There is also a gas inlet tube 71 extending into the container compartment 72 and terminating beneath a pad 73, as previously described. Furthermore, there is an outlet tube 74 alongside the inlet tube 71. A float 76 or float plate normally rests on the pad 73 but is effective to rise if by any chance the liquid level should rise inordinately. The float 76 is substantially disc-shape in plan, as shown in FIG. 4, and has openings 77 to guide it within the container 66 and prevent it from rotating. When the float rises far enough it seats on a shoulder 78 and blocks the entrance to the outlet tube 74. This, as before, prevents the entry of liquid into that tube.

In this instance a special provision is made for permitting the patient to continue receiving gas supplied through the tube 71 even though humidification cannot continue. For that reason there is provided in the inlet tube 71 a number of openings 79 which when open afford free communication between the inlet tube and the outlet tube. However, the shunt passage is normally closed by a check valve 81 in the form of a rubber band. The valve 81 remains shut under normal operating conditions. When the float 76 closes off the entry from the chamber 72 to the outlet tube 74 the differential pressure between the tubes 71 and 74 is sufficient to overcome the tension in the band 81 and to displace the band away from the tube 71, thus opening a shunt path and affording a continuous breathing passage from the inlet tube 71 to the outlet tube 74.

What is claimed is:

1. A respiratory humidifier comprising a base, a heater mounted on said base and having a first heat transfer surface, a container having a second heat transfer surface complementary to said first heat transfer surface, means associated with said base and said container for urging said first heat transfer surface and said second heat transfer surface substantially into abutment, means on said container for admitting liquid to the interior thereof at a lower location near said second heat transfer surface, means for establishing a predetermined liquid level in said container, means on said container for admitting gas to the interior thereof at a location near said second heat transfer surface and below said liquid level, means on said container for releasing gas therefrom at an upper location remote from said second heat transfer surface and above said liquid level, and a pad in and extending substantially completely across said container and disposed between said lower location and said upper location, said pad being permeable throughout to said liquid and to said gas and providing an extended surface for wetting by said liquid and said pad having an upper surface substantially coincident with said liquid level.

2. A device as in claim 1 in which said urging means includes a ring abutting said container and threaded onto said base.

3. A device as in claim 1 in which said liquid admitting means includes means defining an orifice through which said liquid flows, and a float valve in said liquid admitting means for controlling flow of liquid through said orifice to maintain said predetermined level of said liquid in said container.

4. A device as in claim 1 in which said container has a circular-cylindrical interior surface and said pad has a circumferential surface of a diametral size frictionally to engage said interior surface of said container with sufficient force to support said pad substantially at and below said predetermined level of said liquid in said container.

5. A device as in claim 1 including a float plate in said container above said pad and movable into and out of a position blocking flow of said gas from said container through said releasing means.

6. A device as in claim 1 including a shunt passage for gas flow between said gas admitting means and said gas releasing means, and means for normally closing said shunt passage.

7. A device as in claim 6 in which said closing means opens in response to differential pressure when flow of gas from said container through said releasing means is blocked.

8. A respiratory humidifier container comprising a sidewall having an approximately circular-cylindrical interior surface, a metallic bottom wall in liquid-tight engagement with said sidewall, a top engaging said sidewall, liquid admitting means carried by said top and including a tube extending within said container toward said bottom wall, a float valve in said tube for controlling liquid flow therethrough and for maintaining a predetermined level of liquid in said container, gas admitting means carried by said top and including a tube extending within said container toward said bottom wall and below said level, and outlet tube carried by said top and opening to the interior of said container above said level, and a pad having an approximately circular-cylindrical wall of a size frictionally to engage and support said pad on said interior surface, said pad being a relatively thick body of gas-permeable and waterpermeable material having an extended wettable surface and having an upper surface substantially at said level.

* * * * *